United States Patent [19]
Rockley

[11] Patent Number: 6,033,376
[45] Date of Patent: Mar. 7, 2000

[54] WOUND SHAPER SLEEVE

[75] Inventor: Paul W. Rockley, Newport Coast, Calif.

[73] Assignee: Allergan Sales, Inc., Irvine, Calif.

[21] Appl. No.: 09/163,985

[22] Filed: Sep. 30, 1998

[51] Int. Cl.$^7$ .................................................. A61B 17/20
[52] U.S. Cl. .................................. 604/22; 604/35; 604/43
[58] Field of Search ............................ 604/22, 27, 35, 604/43; 138/172

[56] References Cited

U.S. PATENT DOCUMENTS

| | | | |
|---|---|---|---|
| 3,110,753 | 11/1963 | Witort | 138/172 |
| 3,605,725 | 9/1971 | Bentov . | |
| 4,364,394 | 12/1982 | Wilkinson . | |
| 4,461,323 | 7/1984 | Morikawa et al. | 138/172 |
| 4,530,356 | 7/1985 | Helfgott et al. | 128/305 |
| 4,578,059 | 3/1986 | Fabricant et al. . | |
| 4,652,255 | 3/1987 | Martinez . | |
| 4,681,102 | 7/1987 | Bartell | 128/303 R |
| 4,787,889 | 11/1988 | Steppe et al. | 604/22 |
| 4,790,812 | 12/1988 | Hawkins, Jr. et al. . | |
| 4,897,079 | 1/1990 | Zaleski et al. | 604/22 |
| 4,909,249 | 3/1990 | Akkas et al. | 606/107 |
| 4,940,468 | 7/1990 | Petillo | 606/170 |
| 4,983,160 | 1/1991 | Steppe et al. | 604/22 |
| 4,986,827 | 1/1991 | Akkas et al. | 606/107 |
| 5,019,035 | 5/1991 | Missirlian et al. | 604/22 |
| 5,024,654 | 6/1991 | Tyler . | |
| 5,026,393 | 6/1991 | MacKool | 623/6 |
| 5,059,204 | 10/1991 | Lawson et al. | 606/171 |
| 5,084,009 | 1/1992 | MacKool | 604/22 |
| 5,213,569 | 5/1993 | Pauls | 604/22 |
| 5,242,385 | 9/1993 | Strukel | 604/22 |
| 5,257,988 | 11/1993 | L'Esperance | 606/6 |
| 5,282,786 | 2/1994 | Ureche | 604/22 |
| 5,286,256 | 2/1994 | Mackool | 604/22 |
| 5,300,022 | 4/1994 | Klapper et al. . | |
| 5,354,265 | 10/1994 | Mackool | 604/22 |
| 5,364,357 | 11/1994 | Aase | 604/282 |
| 5,472,418 | 12/1995 | Palestrant | 604/43 |
| 5,505,693 | 4/1996 | Mackool | 604/22 |
| 5,569,188 | 10/1996 | Mackool | 604/67 |
| 5,593,394 | 1/1997 | Kanesaka et al. | 604/282 |
| 5,603,703 | 2/1997 | Elsberry et al. . | |
| 5,634,912 | 6/1997 | Injev | 604/264 |
| 5,645,530 | 7/1997 | Boukhny et al. | 604/22 |
| 5,656,029 | 8/1997 | Imran et al. . | |
| 5,685,841 | 11/1997 | Mackool | 604/22 |
| 5,718,676 | 2/1998 | Barrett | 604/22 |
| 5,741,226 | 4/1998 | Strukel et al. . | |
| 5,873,851 | 2/1999 | Nilsson | 604/43 |
| 5,879,356 | 3/1999 | Geuder | 604/22 |

*Primary Examiner*—Ronald K. Stright, Jr.
*Assistant Examiner*—Jeremy Thissell
*Attorney, Agent, or Firm*—Walter A. Hackler

[57] ABSTRACT

A sleeve apparatus for a phacoemulsification/irrigation and aspiration handpiece having an ultrasonic drive assembly attached to a hollow needle includes a compressible sleeve for establishing an annular passage around the needle and enabling the irrigation fluid to pass into an eye through a cornea/sclera wound while cooling the needle. The compressible sleeve includes a wall configuration for controlling compression of the sleeve in order to cause the compressible sleeve to shape and conform to the corneal/sclera wound and limit fluid egress from the wound. A hub is provided for attaching the compressible sleeve to the handpiece and enabling the needle to be angularly displaced within the compressible sleeve means during phacoemulsification.

10 Claims, 1 Drawing Sheet

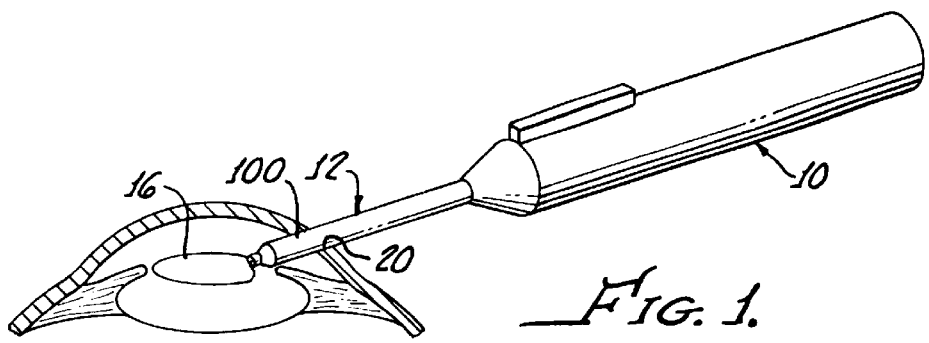
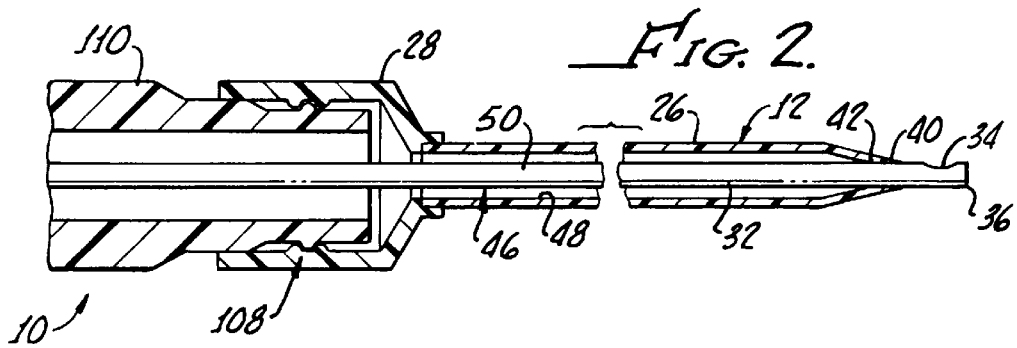
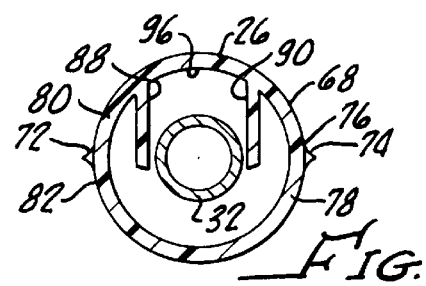
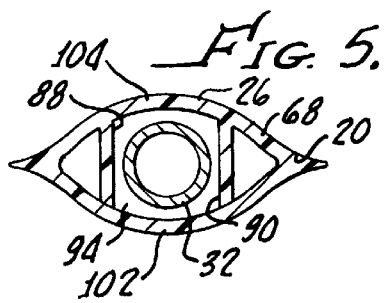
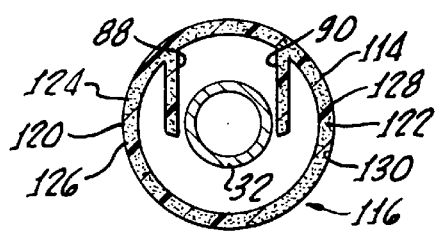
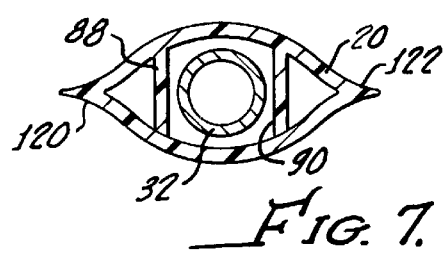

WOUND SHAPER SLEEVE

The present invention generally relates to phacoemulsification handpieces for the removal of a cataract lens from an eye and is more particularly related to sleeve apparatus for a phacoemulsification handpiece.

A well known method for the removal of a cataract through a surgical incision in the eye is known as phacoemulsification. A handpiece for phacoemulsification generally includes an ultrasonic generator which is attached to a hollow needle which is vibrated and, when inserted into an eye, is capable of the emulsion of an eye lens and aspiration thereof through a lumen in the needle. The needle is surrounded by a sleeve when inserted through an incision in the eye. The tip of the needle engages and emulsifies the cataract and a suction force is applied through the needle interior lumen to withdraw the emulsified cataract into the needle and out of the eye.

The sleeve protects the wound through which the needle is passed from contacting the needle which can become heated and the sleeve further establishes an annular passage around the needle for providing an irrigation fluid to the eye while at the same time cooling the needle.

Typically, the cornea or sclera incision is linear and has a length approximately to one-half the circumference of the sleeve in order to minimize fluid leakage from the incision, or wound, when the needle/sleeve is inserted therethrough.

A great number of sleeve designs have been proposed and a number of materials have been utilized in prior art sleeves. For example, U.S. Pat. No. 4,787,889 to Steppe et al, discloses a flexible sleeve made of a synthetic resin such as silicon rubber which is able to fold back or telescope when inserted through an incision. The problems with these prior art devices include collapsing of the flexible sleeve in the area of the wound by pressure from surrounding tissue. This collapsing of the sleeve blocks flow of the irrigation to the surgical site and around the vibrating needle, which can cause overheating and damage to adjacent tissue. Sleeves made out of metallic material, such as also described in the hereinabove referenced U.S. patent, do not allow collapse and, accordingly, allow a greater fluid leakage from the wound.

In order to minimize leakage from the wound past the sleeve, an elliptical sleeve has been proposed, for example, see U.S. Pat. No. 5,084,009. This collapsible, or compressible, sleeve is made with a shape matching the configuration of a surgical incision in order to minimize leakage between the exterior surface of the sleeve and the surgical incision. However, in order for the ultrasonic needle to exhibit a desired and vibratory motion, which is relatively free from damping, this elliptical sleeve must be prohibited from touching the needle during the operation.

During operation procedures, the needle must be partially rotated and its angle of incident changed in order to effect complete phacoemulsification and removal of the lens. In these procedures, a soft sleeve, particularly one shaped to the size of the wound, may collapse, or deflect against the ultrasonic needle. When the sleeve is pushed against the rapidly vibrating needle, the needle and sleeve tend to overheat due to friction, which may damage delicate cornea or sciera tissue, particularly the corneal epithelium.

The present invention is directed to a sleeve which shapes itself to the wound by pressure of surrounding tissue in order to minimize leakage of fluid therepast. In addition, internal structure of the sleeve maintains proper annular channel around the needle for passage of cooling fluid. Accordingly, the needle is prevented from touching the sleeve. In addition, the sleeve is attached to the phacoemulsification handpiece to enable angular motion of the needle within the sleeve so that the sleeve wound junction is not disturbed.

SUMMARY OF THE INVENTION

Sleeve apparatus in accordance with the present invention is suitable for a phacoemulsification handpiece having an ultrasonic drive assembly attached to a hollow needle for emulsifying and aspirating a cataract lens through a cornea/sclera wound.

The subject sleeve apparatus generally includes a compressible sleeve which provides a means for establishing an annular passage around the needle and enabling the irrigation fluid to pass into an eye through the cornea/sclera wound while simultaneously cooling the needle. The compressible sleeve includes a wall configuration which provides a means for controlling compression of the sleeve in order to cause the compressible sleeve to shape and conform to the cornea/sclera wound and limit fluid egress from the wound. That is, the construction of the compressible sleeve wall enables the sleeve, upon compression by tissue subtending the wound, to fill, or contact, all of the wound surface so that no gaps are established which can permit the leakage of fluid.

In addition, a hub means is provided for attaching the compressible sleeve to the handpiece and for enabling the needle to be angularly displaced within the compressible sleeve means. Thus once the compressible sleeve is conformed to the wound shape, it need not be disturbed by subsequent manipulation of the needle which is necessary in order to properly emulsify and aspirate a cataract lens.

In one embodiment of the invention, the compressible sleeve includes a variation in wall thickness around the circumference of the compressible sleeve which may include two areas of the sleeve wall having greater thickness than adjoining areas in the sleeve wall. These two areas are preferably spaced apart from one another at about 180° around the sleeve means circumference. Thus, when the compressible sleeve is inserted into a slit type cornea/sclera wound, the thicker portions of the wall are disposed at opposite ends of the slit and compression of the sleeve enables confirmation of the sleeve with all of the surrounding wound tissue including the ends of the slit.

Still more particularly, the two areas of greater wall thickness may include nodules which extend outward from the compressible sleeve means.

In another embodiment of the present invention, the sleeve may include a variation in wall density of the sleeve walls around the circumference of the sleeve. The variation in wall density preferably includes two areas of the sleeve having a lower density than adjoining areas of the sleeve wall, with the two areas of lower-density being spaced apart from one another at 180° around the sleeve means configuration.

In a manner as similarly described in conjunction with a wall having thicker areas, this lower density area enables a preferential compression of the sleeve and outward extension of the sleeve in the low density wall areas so that the sleeve can conform and contact with all of the tissue surrounding the slit wound.

Also, in accordance with the present invention, in order to limit compression of opposing walls of the compressive sleeve to prevent contact of the compressible sleeve with the needle, depending member means are provided. In addition to preventing contact of the compressible sleeve with the needle, the depending member means maintains an annular passage for flow of irrigation fluid past the needle. As a result, continued cooling of the needle is ensured at all times.

More particularly, the depending member means includes members, having a length greater than the diameter of the needle, are disposed within the compressible sleeve and are attached to opposing walls between the two wall areas of greater thickness, or lesser density.

BRIEF DESCRIPTION OF THE DRAWINGS

The present invention may be more clearly appreciated when taken in conjunction with the accompanying drawings, in which:

FIG. 1 is a perspective view of a phacoemulsification handpiece using the sleeve apparatus in accordance with the present invention as it may be inserted through a cornea/sclera wound for the removal of a cataract lens from a lens capsule;

FIG. 2 is a cross sectional view of the sleeve apparatus in accordance with the present invention including a compressible sleeve and hub for attaching the sleeve to the phacoemulsification handpiece;

FIG. 3 is a cross sectional view of a prior art sleeve as inserted into a slit type wound illustrating the problem with regard to gaps being created by such insertion which provide a means for fluid egress from the eye during the phacoemulsification procedure;

FIG. 4 is a cross sectional view of one embodiment of the present invention showing a compressible sleeve having side walls of greater thickness disposed in an opposing relationship around the compressible sleeve along with a pair of depending members which are provided for limiting the collapse of the collapsible sleeve;

FIG. 5 is the collapsible sleeve as shown in FIG. 4 shown inserted into a slit type cornea/sclera wound, with the outside, or perimeter, of the collapsible sleeve conforming exactly to the slit opening upon compression of the sleeve so that little or no gaps are established for the egress of fluid;

FIG. 6 is an alternative embodiment of the present invention in which side walls include a lower density in opposing walls for enabling preferential collapse of the collapsible sleeve; and FIG. 7 show the sleeve as shown in FIG. 6 as it conforms to a slit cornea/sclera wound.

DETAILED DESCRIPTION OF THE DRAWINGS

With reference to FIG. 1, there is shown a phacoemulsification handpiece 10 utilizing sleeve apparatus 12 in accordance with the present invention for removing a cataract lens 16 by emulsification/aspiration through a cornea/sclera wound 20. The phaco handpiece, or instrument 10, may be of any conventional type operating, as is well known to those skilled in the art, except as modified with the sleeve apparatus 12 in accordance with the present invention.

As more clearly shown in FIG. 2, the sleeve apparatus 12 in accordance with the present invention, includes a sleeve 26 and a hub 28 fixed thereto. It should be appreciated that the sleeve 26 and hub 28 may be formed from the same type of material, for example, a silicone or silicone-type material or of a thermoplastic polyurethane and that the sleeve 26 and the hub 28 may be either fixed to one another or formed integrally.

The handpiece 10 includes an ultrasonic drive assembly, not shown, attached to a hollow needle 32, which includes at least one port 34 disposed in an end 36 of the needle 32, the end 36 protruding through a sleeve 26 at a distal end 40 with a seal 42 disposed therebetween.

As shown, an annular passage 46 is established between an inside surface 48 of the sleeve 28 and an outside surface 50 of the needle 32 in order to enable irrigation fluid provided by the handpiece to pass around the needle 32 and through the port 34 in a conventional manner. The fluid interconnection between the annular passage 46 and the handpiece is not shown, as this arrangement is well known in the art.

It is important, during a phacoemulsification procedure, that tissue surrounding the cornea/sclera wound 20 not be damaged, particularly the epithelium layer under the cornea. Since damage to this tissue may occur due to heating, a prior art sleeve 56, see FIG. 3, has been typically provided with sufficient resiliency in order to prevent total collapse of the sleeve 56 in order to maintain a fluid conduit 58 between the sleeve 56 and the needle 32. While aspiration of cataractic tissue, not shown, is performed through a needle lumen 60, sufficient cooling is only provided by the irrigation of fluid passing through the passage 58. It must also be appreciated that this size of the needle 32 and sleeve 58 is quite small, since the length of the slit cornea/sclera wound may be only about 3 mm.

Not only is it important that the passage 58 be maintained for cooling of the needle, it is also important that the needle 32 does not contact the sleeve 56 because conductive heat transfer to the tissue surrounding the wound 20 would cause undesired heating.

The rigidity or relative rigidity of the prior art sleeve 56, as is necessitated by the constraints hereinabove set forth, preclude the sleeve 56 from shaping, or conforming, to the slit wound 20. Rather, gaps 64 between the sleeve 56 and the wound 20 occur which enable leakage of irrigation fluid therepast. This leakage is undesirable, as is well known in the art, because it interferes with proper maintenance of ocular pressure during the phacoemulsification procedure.

As shown in FIGS. 4 and 5, the sleeve 26 in accordance with the present invention, overcomes the deficiencies of the prior art, sleeve 56 by incorporating a sleeve wall which provides a means for controlling compression of the sleeve 26 in order to cause the compressible sleeve 26 to shape and conform to the cornea/sclera wound 20, thus limiting fluid egress from the wound, see FIG. 5.

Referring again to FIG. 4, a variation in sleeve wall 68 thickness is provided in two areas, 72, 74 around the sleeve 26 and preferably spaced apart from one another at a 180° angle in order to enable the sleeve 26 to shape and conform to the cornea/sclera wound 20 as shown in FIG. 5.

Because the areas 72, 74 are thicker than adjacent areas 76, 78, 80, 82, respectively, controlled collapse of the sleeve 26 under pressure of surrounding tissue, not shown in FIG. 4, is provided. In order to further enhance sealing between the sleeve 26 and the wound 20, the thicker areas may be in the form of nodules 72, 74. In this manner, the sleeve 26 completely shapes, or conforms, to the wound 20 as shown in FIG. 5.

In order to prevent the compression, or collapse of the sleeve onto the needle 32, depending member means 88, 90, are provided. With a length greater than a diameter of the needle 32, the depending member means 88, 90 prevent contact of the sleeve 26 with the needle 32 and maintain an annular passage 94 therebetween, see FIG. 5.

The depending members 88, 90 may be formed of the same material as the sleeve and intricately formed thereto. It should also be appreciated that the members 88, 90 need only be present on an inside of a surface 96 of the sleeve 26 in an area 100 of the sleeve passing through the wound 20, see FIG. 1.

The depending members 88, 90 may be attached to opposing walls 102, 104 of the sleeve 26 which will result in the same compressed configuration as shown in FIG. 5.

Because of the important conformation of the sleeve 26 with the wound 20, rotation of the sleeve within the wound 20 is not desirable. Accordingly, in order to enable the needle 32 to be angularly displaced within the compressible sleeve 26, the hub includes conventional snap fittings 108 which enable rotation of the hub 28 and sleeve about a handpiece body 110. Thus the hub 28 and sleeve 26 may be held in an orientation affording proper shaping of the sleeve 26 with the wound 20, while the needle is angularly moved within the sleeve and further axially tilted within the wound 20 in order to effect a proper emulsification of the lens 16 and aspiration thereof through the needle lumen 60.

As hereinabove discussed, it is important that the sleeve 26 includes wall means 68 for controlling compression of the sleeve 26 and in that regard, an alternate wall means 114 may be provided for an alternate sleeve 116 as shown in FIG. 6. In this embodiment, the wall 114 includes areas of a lower density 120, 122 surrounded by areas 124, 126, 128, 130 of heavier density which enables collapse of the sleeve upon compression by surrounding wound tissue so that the sleeve 116 takes the shape and conforms to the wound 20 as shown in FIG. 7. Hence, the many gaps, not shown, are not established between the sleeve 116 and the wound 20 in order to prevent undesirable egress of irrigation fluid as hereinabove discussed. Dependent members 88, 90 are also provided within the sleeve 116 and function in a manner identical to the members 88, 90, shown in FIGS. 4 and 5.

Although there has been hereinabove described specific embodiments of wound shaper sleeve apparatus, in accordance with the present invention, for the purpose of illustrating the manner in which the invention may be used to advantage, it should be appreciated that the invention is not limited thereto. Accordingly, any and all embodiments, variations, or equivalent arrangements which may occur to those skilled in the art, should be considered to be within the scope of the present invention as defined in the appended claims.

What is claimed is:

1. Sleeve apparatus for a phacoemulsification/irrigation and aspiration handpiece having an ultrasonic drive assembly attached to a hollow needle for emulsifying and aspirating a cataract lens through a cornea/sclera wound, said sleeve apparatus comprising:

compressible sleeve means for establishing an annular passage around the needle and enabling irrigation fluid to pass into an eye through the cornea/sclera wound while cooling the needle; and depending member means disposed within said compressible sleeve means, for limiting compression of opposing walls of said compressible sleeve means in order to prevent contact of said compressible sleeve means with said needle and maintain the annular passage for flow of irrigation fluid past said needle;

hub means for attaching said compressible sleeve means to the handpiece and for enabling the needle to be angularly displaced within said compressible sleeve means.

2. The sleeve apparatus according to claim 1 wherein said depending member means have a length greater than a diameter of said needle.

3. Sleeve apparatus phacoemulsification/irrigation and aspiration handpiece having an ultrasonic drive assembly attached to a hollow needle for emulsifying and aspirating a cataract lens through a corneal/sclera wound, said sleeve apparatus comprising:

compressible sleeve means for establishing an annular passage around the needle and enabling irrigation fluid to pass into an eye through the cornea/sclera wound while cooling the needle, said compressible sleeve means including wall means for controlling compression of the sleeve means in order to cause said compressible sleeve means to shape and conform to the corneal/sclera wound and limit fluid egress from the wound, said wall means including a variation in wall thickness of said compressible sleeve means around a circumference of said compressible sleeve means, said variation in wall thickness comprising two areas of sleeve means wall having greater thickness than adjoining areas of sleeve means wall, the two areas being spaced apart from one another at 180° around the sleeve means circumference;

depending member means, disposed within said compressible sleeve means and attached to opposing walls of the sleeve means between the two areas, for limiting compression of the opposing walls in order to prevent contact of said compressible sleeve means with said needle and maintain annular flow of irrigation fluid past said needle and hub means for attaching said compressible sleeve means to the handpiece for enabling the needle to be angularly displaced within said compressible sleeve means.

4. The sleeve apparatus according to claim 3 wherein said depending member means has a length greater than a diameter of said needle.

5. Sleeve apparatus for a phacoemulsification/irrigation and aspiration handpiece having an ultrasonic drive assembly attached to a hollow needle for emulsifying and aspirating a cataract lens through a corneal/sclera wound, said sleeve apparatus comprising:

compressible sleeve means for establishing an annular passage around the needle and enabling irrigation fluid to pass into an eye through the cornea/sclera wound while cooling the needle, said compressible sleeve means including wall means for controlling compression of the sleeve means in order to cause said compressible sleeve means to shape and conform to the corneal/sclera wound and limit fluid egress from the wound, said wall means including a variation in wall density of said compressible sleeve means around a circumference of said compressible sleeve means, said variation in wall density comprising two areas of sleeve means wall having a lower density than adjoining areas of sleeve means wall, the two areas being spaced apart from one another at 180° around the sleeve means circumference;

depending member means, disposed within said compressible sleeve and attached to opposing walls of the sleeve means between the two area, for limiting compression of the opposing walls in order to prevent contact of said compressible sleeve means with said needle and maintain an annular flow of irrigation fluid past said needle; and hub means for attaching said compressible sleeve means to the handpiece and for enabling the needle to be angularly displaced within said compressible sleeve means.

6. The sleeve apparatus according to claims 1, 3 or 5 wherein said depending member means comprises two depending members, said needle being disposed between said two depending members.

7. The sleeve apparatus according to claim 6 wherein said compressible sleeve means has a cylindrical shape before compression by the cornea/sclera wound.

8. The sleeve apparatus according to claim 5 wherein said depending member means has a length greater than a diameter of said needle.

9. Sleeve apparatus for a phacoemulsification/irrigation and aspiration handpiece having an ultrasonic drive assembly attached to a hollow needle for emulsifying and aspirating a cataract lens through a corneal/sclera wound, said sleeve apparatus comprising:

a compressible sleeve for establishing an annular passage around the needle and enabling irrigation fluid to pass into an eve through the corneal/sclera wound while cooling the needle, said compressible sleeve means having an initial uncompressed circular inside diameter, said compressible sleeve including a wall for controlling compression of the sleeve in order to cause said compressible sleeve to shape and conform from the initial circular diameter to the cornea/sclera wound and limit fluid egress from the wound;

depending members disposed within said compressible sleeve, for limiting compression of opposing walls of said compressible sleeve in order to prevent contact of said compressible sleeve with said needle and moisten annular flow of irrigation fluid past said needle; and a hub for attaching said compressible sleeve to the handpiece and for enabling the needle to be angularly displaced within said compressible sleeve.

10. The sleeve apparatus according to claim 9 wherein said depending members have a length greater than a diameter of said needle.

* * * * *